United States Patent
Tsukada et al.

(10) Patent No.: US 6,842,637 B2
(45) Date of Patent: *Jan. 11, 2005

(54) MAGNETIC FIELD MEASUREMENT APPARATUS

(75) Inventors: Keiji Tsukada, Kashiwa (JP); Akihiko Kandori, Hachioji (JP); Tsuyoshi Miyashita, Kokubunji (JP); Hiroyuki Suzuki, Hitachinaka (JP); Hitoshi Sasabuchi, Mito (JP)

(73) Assignee: Hitachi, Ltd., Tokyo (JP)

( * ) Notice: Subject to any disclaimer, the term of this patent is extended or adjusted under 35 U.S.C. 154(b) by 305 days.

This patent is subject to a terminal disclaimer.

(21) Appl. No.: 09/948,857

(22) Filed: Sep. 10, 2001

(65) Prior Publication Data

US 2002/0019589 A1 Feb. 14, 2002

Related U.S. Application Data

(63) Continuation of application No. 09/176,767, filed on Oct. 22, 1998, now Pat. No. 6,424,853.

(30) Foreign Application Priority Data

Oct. 24, 1997 (JP) .............................. 9-292025

(51) Int. Cl.⁷ ................................ A61B 5/05
(52) U.S. Cl. ..................... 600/409; 600/407; 600/410; 600/422; 600/423; 323/43
(58) Field of Search ............................... 600/409, 407, 600/410, 422, 423, 523, 524, 440, 569, 509; 323/43

(56) References Cited

U.S. PATENT DOCUMENTS 4,324,255 A * 4/1982 Barach et al. .............. 600/300
4,793,355 A * 12/1988 Crum et al. ................ 600/409

(List continued on next page.)

FOREIGN PATENT DOCUMENTS

| JP | 2-116767 | 5/1990 |
|----|----------|--------|
| JP | 5-146416 | 6/1993 |
| JP | 05-196711 | 8/1993 |
| JP | 7-148131 | 6/1995 |
| JP | 08-071051 | 3/1996 |

OTHER PUBLICATIONS

Review of Scientific Instruments, vol. 66, No. 10, Oct. 1995, "Multi-channel SQUID system detecting tangential components of the cardiac magnetic field", K. Tsukada et al, pp. 5085–5091.

10th International Conference on Biomagnetism BIOMAG96, 1996, "A 129 Channel Vector Neuromagnetic Imaging System", Y. Yoshida et al, p. 351.

Primary Examiner—Angela D. Sykes
Assistant Examiner—William C. Jung
(74) Attorney, Agent, or Firm—Mattingly, Stanger & Malur, P.C.

(57) ABSTRACT

A magnetic field measurement apparatus includes a plurality of magnetometers each having SQUID's and three detection coils, one of which detects each of three orthogonal directional magnetic field components ($B_x$, $B_y$, $B_z$) of a magnetic field generated from a subject to be inspected, a display which displays time variation of waveforms of the magnitude ($\sqrt{(B_x^2+B_y^2+B_z^2)}$) of magnetic field synthesized by square sum of each of the three orthogonal directional magnetic field components of the magnetic field generated from the subject to be inspected, a holder for holding a Dewar's vessel for arranging magnetometers therein, and a controller for controlling a positional relationship between the subject to be inspected and the Dewar's vessel. Accurate time variation of the magnetic field generated from the subject to be inspected can be detected without influence of positional change of the subject to be inspected, by simultaneously measuring each of the three orthogonal directional magnetic field components ($B_x$, $B_y$, $B_z$) of the magnetic field generated from current sources in the subject to be inspected.

4 Claims, 15 Drawing Sheets

U.S. PATENT DOCUMENTS

| | | | |
|---|---|---|---|
| 4,951,674 A | * 8/1990 | Zanakis et al. | 600/409 |
| 4,995,165 A | 2/1991 | Daniels | 33/361 |
| 4,995,395 A | 2/1991 | Ilmoniemi et al. | 128/653.1 |
| 5,027,819 A | 7/1991 | Crum | 128/653.1 |
| 5,274,582 A | * 12/1993 | Whitby | 708/807 |
| 5,291,135 A | * 3/1994 | Hotta et al. | 324/248 |
| 5,471,985 A | 12/1995 | Warden | 128/653.1 |
| 5,644,229 A | 7/1997 | Dossel et al. | 324/247 |
| 5,657,756 A | * 8/1997 | Vrba et al. | 600/409 |
| 5,752,514 A | * 5/1998 | Okamura et al. | 600/409 |
| 5,755,227 A | * 5/1998 | Tomita et al. | 600/407 |
| 5,880,588 A | * 3/1999 | Kado | 324/248 |
| 5,894,220 A | 4/1999 | Wellstood et al. | 324/248 |

* cited by examiner

MAGNETIC FIELD MEASUREMENT APPARATUS

This is a continuation application of U.S. Ser. No. 09/176,767, filed Oct. 22, 1998 now U.S. Pat. No. 6,424,853.

BACKGROUND OF THE INVENTION

1. Field of the Invention

The present invention relates to a magnetic field measurement apparatus consisting of a magnetometer comprised of a Superconductive Quantum Interferometer Device (SQUID) for measuring magnetic fields generated by the nervous activity of the brain of humans or animals or myocardial activity or magnetic substances contained in the subject to be inspected.

2. Description of Related Art

In measurements of very weak magnetic fields in the conventional art using equipment such as SQUID for measuring biomagnetic fields, generally the magnetic field on the surface of a living body is capable of being measured. Such measurements can be just the vertical components of a magnetic field with the head regarded as a sphere, for instance the polar coordinates $(r, \phi, \theta)$ in the case of the head, and the magnetic field component Br in the vertical r direction on the head surface, or in the case of the heart, the orthogonal coordinates $(X, Y, Z)$, of the chest section when measured on the flat planes X and Y, and the magnetic field component $B_Z$. in the vertical Z direction on the X and Y planes.

On the other hand while few in number, there is literature reporting on measurement apparatus for measuring magnetic components of a biomagnetic field in a plurality of directions. For instance, the simultaneous measurement of the magnetic component $B_X$ in the X direction and the magnetic component $B_Y$ in the Y direction on the orthogonal coordinates $(X, Y, Z)$; as well as the display of magnitude $\sqrt{(B_X^2 + B_Y^2)}$ synthesized by magnetic component $B_X$ in the X direction and magnetic component $B_Y$ in the Y direction have been reported (K. Tsukada et. al., Rev. Sci. Instrum., 66 (10), pp 5085–5091(1995)).

Further, though not the three directions $B_r$, $B_\phi$, $B_\theta$ of the polar coordinates $(r, \phi, \theta)$ of the magnetic components $B_X$, $B_Y$ and $B_Z$ in the three directions of the orthogonal coordinates $(X, Y, Z)$; a method has been reported for measuring the three components of each intersecting magnetic field, finding the magnetic components $B_r$, $B_\phi$, $B_\theta$ in the three directions on the polar coordinates $(r, \phi, \theta)$ and displaying a waveform showing the time variation of each magnetic component in three directions on polar coordinates $(r, \phi, \theta)$ on a CRT screen (Y. Yoshida et. al., 10th Int'l Conf. on Biomagnetisim (1996)).

Also, in the conventional art, not only a waveform showing time variations in a magnetic field strength but also the distribution of the magnitude of a magnetic field can be found from results of magnetic measurements of a plurality of points in an organism utilizing a plurality of magnetometers and the result displayed as a magnetic field magnitude contour map. Factors such as the position, magnitude and direction of electrical current sources in an organism can be analyzed over desired periods of time on a magnetic field contour map and changes over time in the electrical physiological phenomenon in the organism thus discovered. In the conventional art, changes in electrical physiological phenomenon in a dynamic organism can therefore be revealed by utilizing these magnetic field contour maps to aid in the diagnosis of disease.

In the method used in the conventional art, the heart of the child or adult which is the subject of measurement is fixed in a constant position and direction versus the magnetic plane of the magnetic field of the magnetometer. However, there is the problem that when measuring the magnetic field of the heart of a fetus, an accurate measurement of the heart's magnetic field cannot be made since the position and direction of the fetus cannot be fixed since the fetus is constantly moving within the body of the mother. In other words, even if there is no change in the electrical current source within the heart of the fetus the position and direction will change versus the magnetic plane of the magnetic field generated in the magnetometer by the heart of the fetus creating the problem that the time waveform and the components of the magnetic field being measured cannot be fixed. Another problem in the conventional art, is that a standardized waveform cannot be obtained due to variations in the magnetic field waveform due to changes in the body position of the fetus within the body of the mother, making an accurate diagnosis of the heart disease of the fetus difficult. Further, when the position of the Dewar's vessel housing the magnetometer is moved in order to increase the magnetic signal to measure the component in just one direction of the magnetic field, the magnetic signal reaches a maximum and the measurement range narrows so that setting an ideal position and direction for measurement with the Dewar's vessel is difficult creating the problem that a long time is required. A still further problem is that a large drift occurs in the magnetic signal being detected when moving the Dewar's vessel to an optimal position versus the subject being measured and a long time is thus required to stabilize the magnetic signal being detected.

Yet another problem is that high sensitivity nondestructive inspection of minute impurities having magnetic properties within a nonmagnetic substance is difficult and furthermore the investigation cannot be conducted with high speed.

SUMMARY OF THE INVENTION

In order to resolve the above mentioned problems, it is therefore an object of this invention to provide a magnetic field measurement apparatus and a magnetic field measurement method for accurately measuring the electrical physiological phenomenon within the heart of a fetus without affecting a change in the status of the fetus even when the direction and position of the fetus changes within the body of the mother. It is a further object of the invention to provide a magnetic field measurement apparatus and a magnetic field measurement method for accurately detecting changes over time in the magnetic field from the subject of inspection even in cases where a position change has occurred in the subject for inspection while placed in an environment for inspection or the subject for inspection is placed inside a special material for inspection.

The magnetic field measurement apparatus of this invention is comprised of a detection coils for detecting magnetic fields of three directions and a superconductive quantum interferometer device (SQUID) connected to these detection coils; a single or a plurality of vector magnetometers are provided for isolating and measuring each of the magnetic components for the three directions. The magnetic components of the intersecting three directions measured with the single or plurality of vector magnetometers are synthesized by the square sum method and a time waveform of the resulting magnitude of the magnetic field is shown on a display means (monitor).

In the magnetic field measurement apparatus of this invention, a holding means and control means for storing and cooling the vector magnetometers, maintaining the vector magnetometers in a superconductive state in the Dewar's vessel and varying the direction of the center position of the bottom of the Dewar's vessel towards the subject for inspection is provided. The center position of the bottom of the Dewar's vessel is set to an ideal position and direction versus the subject for inspection so that the magnitude of the time waveform reaches a maximum, while observing time waveform on the monitor. When shifting the bottom of the Dewar's vessel for optimum direction and position while watching the monitor, and the frequency band width of the magnetic field being measured is widened, time is required for the signal drift to significantly stabilize so that in order to remove the drift of the output waveform when moving the Dewar's vessel, the signal from each magnetometer is split into two signal. One of these signals is fed to a highpass filter, the signal then processed and then displayed on the monitor. The other signal is input to a data analysis and storage device such as a personal computer.

The magnetic components of the three directions are $B_X$, $B_Y$, $B_Z$ of the three directions of the orthogonal coordinate system (X, Y, Z): are $B_r$, $B_\phi$, $B_\theta$ of magnetic components of the three directions (r, ø, θ) of the polar coordinate system. The magnetic components $B_r$, $B_\phi$, $B_\theta$ are converted into the magnetic components $B_X$, $B_Y$, $B_Z$ of the three directions. A coil bobbin made from highly polymerized resin insulating piece such as glass fiber reinforced epoxy resin, fiber reinforced plastic (FRP) or PEEK is mounted with detection coils in three intersecting directions and made from super conductive material for isolating and detecting the direction of magnetic fields having different mutually intersecting surfaces, and comprising a vector magnetometer for measuring $B_X$, $B_Y$, $B_Z$ simultaneously. The center of the surface forming the three detection coils is provided along the center of the bobbin. Further, a surface forming one detection coil is perpendicular to the center axis of the coil bobbin. The surfaces forming the other two detection coils intersect and are also parallel to the center axis of the coil bobbin.

The intensity (magnitude) of the magnetic field vector expressing a synthesis of $\sqrt{(B_X^2+B_Y^2+B_Z^2)}$ is found from the magnetic components $B_X$, $B_Y$, $B_Z$ of the three directions simultaneously measured by using the vector magnetometers and shown as a magnetic field magnitude distribution graph on the display means. Changes over time of the intensity of the magnetic vectors are then monitored.

In this invention therefore, the magnetic components of the three intersecting directions formed by the electrical current source generated by the subject being examined are all simultaneously measured, a squared sum taken of the three directions of the magnetic components is displayed on a time waveform so that virtually no difference occurs in the detection position of the magnetic field of the subject under examination and having the effect that changes over time in the magnetic field can be accurately detected. Consequently, a wide range can be set for detecting the position and detection of the subject for measurement by the magnetometer housed in the Dewar's vessel and measurements can be made of high signal-to-noise (S/N) ratios since large signals can be detected. There are virtually no differences in the time waveform due to differences in the detection position of the magnetic field of the subject for measurement and a time waveform with nearly the same magnetic field can be obtained in a wide region for the subject being measured so that when for instance, the essential subject for measurement is the fetus inside the body of the mother, then variations in the magnetic signal detected due to changes in the positional relationship can be reduced even if changes occur in the positional relationship of mother and fetus. Accordingly, the influence of changes in the magnetic signal due to the detection position of the magnetic field are small and the status of the heart of the fetus can be accurately determined. Also, by passing the signal of each magnetic component of the three directions through a high pass filter, the time required of the detected magnetic signal to stabilize is shortened and measurement can be speeded up since the point where the magnetic signal is greatest can be detected within a short time.

A summary of this invention is described next. A magnetic field measurement apparatus has a plurality of magnetometers comprised of a superconductive quantum interferometer device and detection coils for detecting the magnetic components ($B_X$, $B_Y$, $B_Z$) of the three intersecting directions of the magnetic field generated by the subject for measurement, a display means for displaying a time waveform of the magnetic field intensity synthesized from the magnetic field components detected by the magnetometers, a holding means for maintaining the Dewar's vessel housing the magnetometers, a control means for controlling the positional relation of the Dewar's vessel and the subject for measurement, and a display means for displaying changes over time in the intensity (magnitude) $\sqrt{(B_X^2+B_Y^2+B_Z^2)}$ of the magnetic field vector expressing a synthesis of results found from taking the squared sum of the magnetic components of the three directions. Thus no effects are sustained from positional changes of the subject for measurement the magnetic components of the three directions formed by the electrical current source of the subject for measurement are measured simultaneously, and accurate changes over time in a magnetic field can be detected.

The outline of this invention is as follows. A magnetic field measurement apparatus comprises a plurality of magnetometers each comprising SQUID's and three detection coils each of which detects each of three orthogonal directional magnetic field components ($B_X$, $B_Y$, $B_Z$) of a magnetic field generated from a subject to be inspected, a display which displays time variation of wave form of magnitude $\{\sqrt{(B_X^2, B_Y^2, B_Z^2)}\}$ of magnetic field synthesized by square sum of each of the three orthogonal directional magnetic field components of the magnetic field generated from the subject to be inspected, a holding means for holding Dewar's vessel for arranging magnetometers therein, and a controlling means for controlling a positional relationship between the subject to be inspected and the Dewar's vessel. Accurate time variation of magnetic field generated from the subject to be inspected can be detected without influence of positional change of the subject to be inspected, by simultaneously measuring each of three orthogonal directional magnetic field components ($B_X$, $B_Y$, $B_Z$) of a magnetic field generated from current sources in the subject to be inspected.

DETAILED DESCRIPTION OF THE PREFERRED EMBODIMENTS

The present invention will now be described in detail while referring to the accompanying drawings.

First Embodiment

Figure 1:
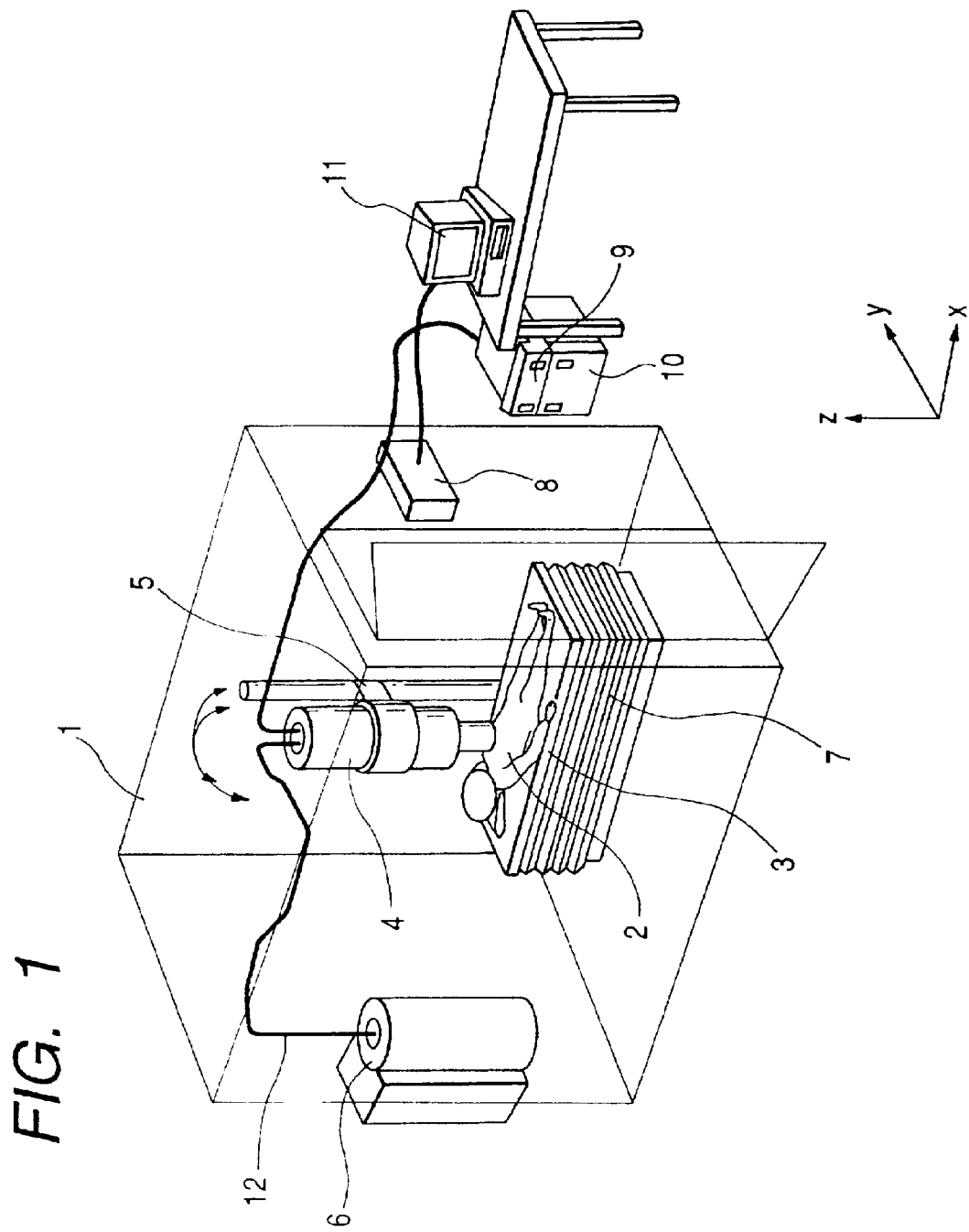
FIG. 1 is a drawing showing the layout of the magnetic field measurement apparatus of the first embodiment of this invention.

FIG. 1 is a drawing showing the layout of the magnetic measurement apparatus for measuring the magnetic field generated from the heart of the fetus. The magnetic field generated from the heart of the fetus is very weak so measurements were performed in a magnetically shielded room to prevent effects from environmental magnetic noise. The mother's body 2 containing the fetus is made to lie down in a bed 3. A vector magnetometer consisting of detection coils integrated with a SQUID for simultaneously detecting magnetic field components in three directions as well as a Dewar's vessel 4 for storing the coolant (liquid helium) for maintaining the superconductive state of the vector magnetometers were positioned above the belly of the mother's body 2. A holding means 5 for holding the Dewar's vessel 4 and having a mechanism for changing the position and angle of the bottom of the Dewar's vessel 4 is capable of changing the angle of the bottom of the Dewar's vessel 4 versus the belly of the mother's body 2. The center axis y of the Dewar's vessel 4 usually parallels the Z axis shown in FIG. 1 however as shown by the direction of the two arrows in FIG. 1, the center axis y of the Dewar's vessel 4 is capable of moving within the plane of the XZ surface as well as the ZY surface. An automatic helium refill device 6 is installed outside the shielded room 1 to refill by way of the transfer tube 12, an amount of liquid helium just equal to the amount evaporated from the Dewar's vessel 4. Also, an elevating mechanism 7 for the bed 3 is capable of varying the distance between the Dewar's vessel 4 and the belly of the mother's body 2.

A display means 8 comprised of a liquid crystal display panel is mounted on an inner wall of the shielded room 8 and the angle and position of the bottom of the Dewar's vessel 4 is changed as needed while monitoring the time waveform on the display means 8. The vector magnetometers are connected to the FLL (Flux Locked Loop) circuit 9 and a proportional voltage output obtained for the three detected directions. The voltage output of the FLL circuit 9 is amplified in an amp filter unit 10, the frequency band selected, A/D conversion performed and the result input to a computer 11. The A/D converted magnetic field signal is processed in the computer 11 according to the description in the following embodiment and the results of the processing shown on the display of the computer 11 and the display means 8.

Second Embodiment

Figure 2:
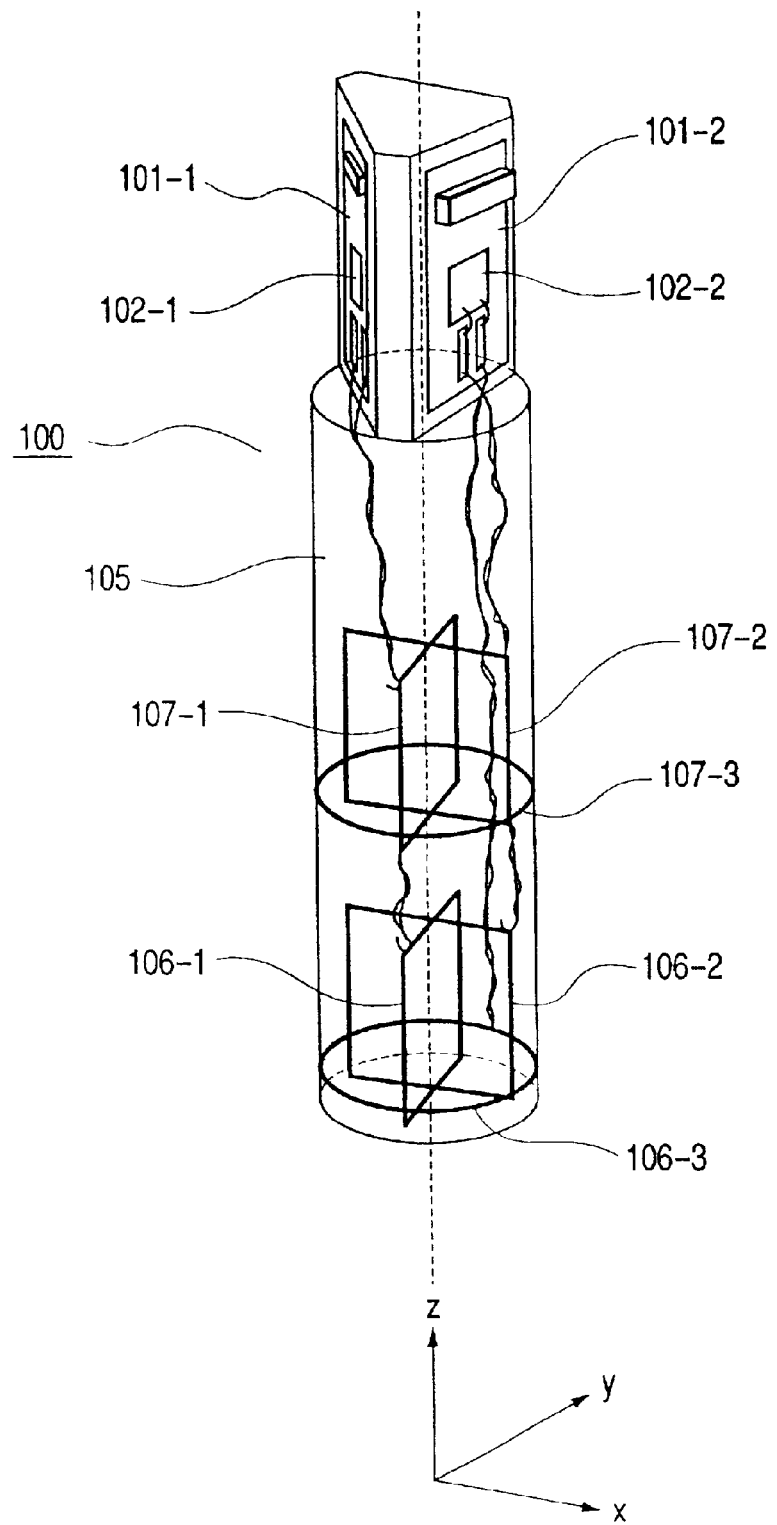
FIG. 2 is a drawing showing the structure of the vector magnetometer of the second embodiment of this invention.

FIG. 2 is a drawing showing the structure of the vector magnetometer 100. The vector magnetometer 100 comprises a detection coil for detecting $B_X$ along the X axis of the magnetic field, a detection coil for detecting $B_Y$ along the Y axis of the magnetic field, and a detection coil for detecting $B_Z$ along the Z axis of the magnetic field and is capable of simultaneously detecting the magnetic fields $B_X$, $B_Y$, $B_Z$ in the three directions when set along the XY plane of (X, Y, Z) of the orthogonal coordinate system of a bed 3. Each of the coils for detecting the three directions of the magnetic fields $B_X$, $B_Y$, $B_Z$ are integrated into one piece with a coil bobbin 105.

In FIG. 2, one tubular shaped coil bobbin 105 is arranged in the Z direction along the longitudinal axis. The three detection coils 106-1, 106-2, 106-3 for detecting the three directions of the magnetic fields are installed in the coil bobbin 105. Compensation coils 107-1, 107-2, 107,3 for canceling out environmental magnetic noise are installed in the upper part of the coil bobbin 105 at a position farther than the detection coils from the subject for measurement (the subject for measurement is at the bottom of FIG. 2). The detection coils are comprised of a detection coil 106-1 for detecting $B_X$ (X direction of magnetic field), a detection coil 106-2 for detecting $B_Y$ (Y direction of magnetic field), and detection coil 106-3 for detecting $B_Z$ (Z direction of magnetic field). The compensation coils are comprised of a compensation coil 107-1 for compensating the X component of environmental magnetic noise, a compensation coil 107-2 for compensating the Y component of environmental magnetic noise, and a compensation coil 107-3 for compensating the Z component of environmental magnetic noise.

Figure 3:
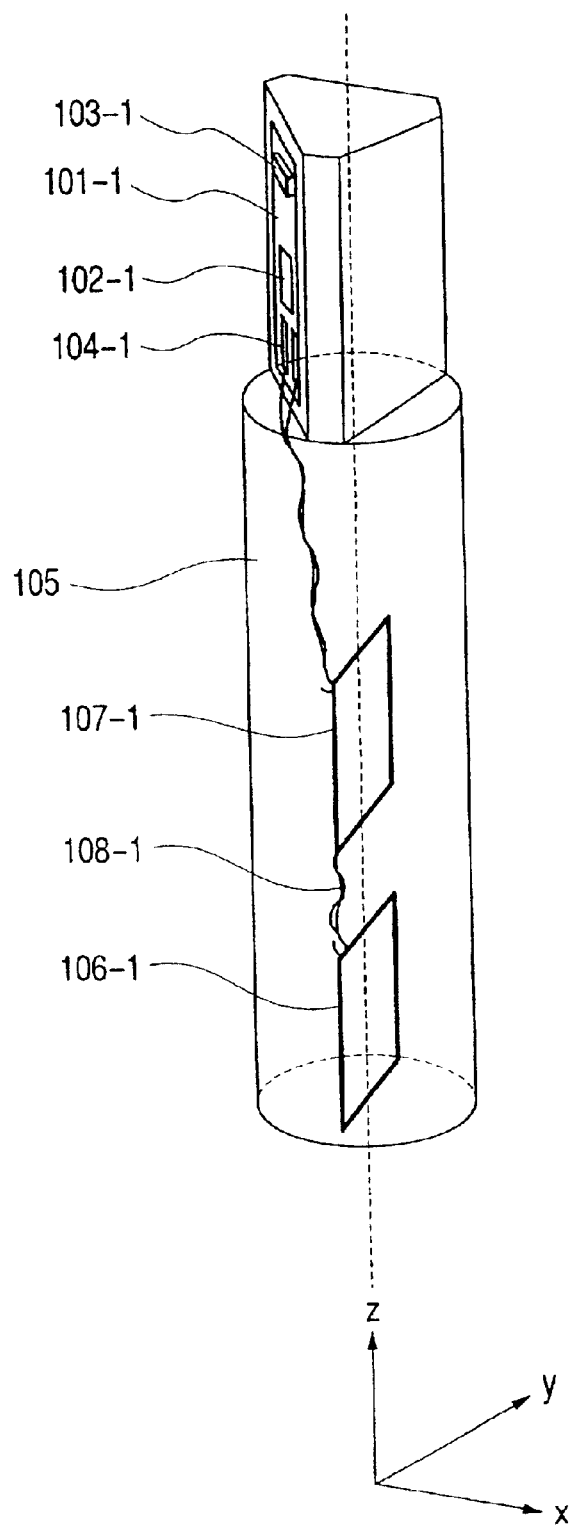
FIG. 3 is a drawing showing the structure of the vector magnetometer of the second embodiment of this invention.
Figure 4:
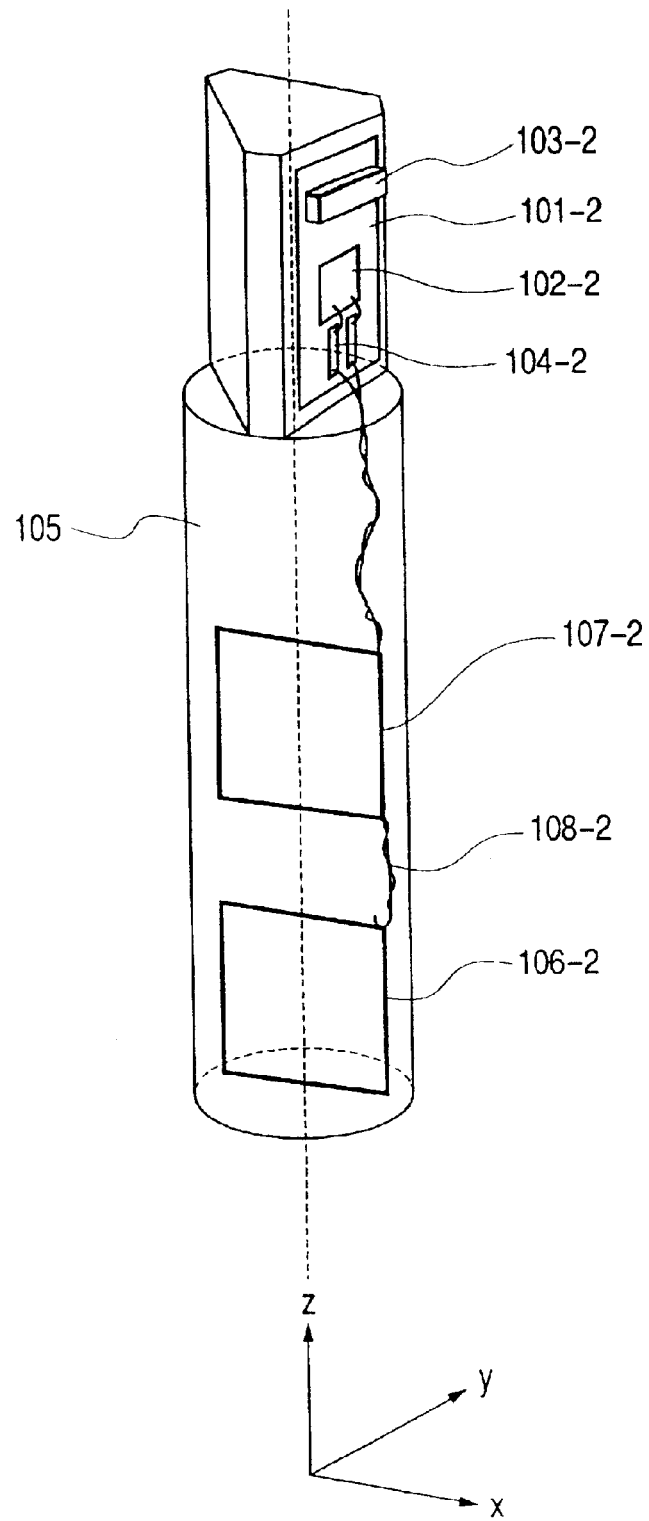
FIG. 4 is a drawing showing the structure of the vector magnetometer of the second embodiment of this invention.
Figure 5:
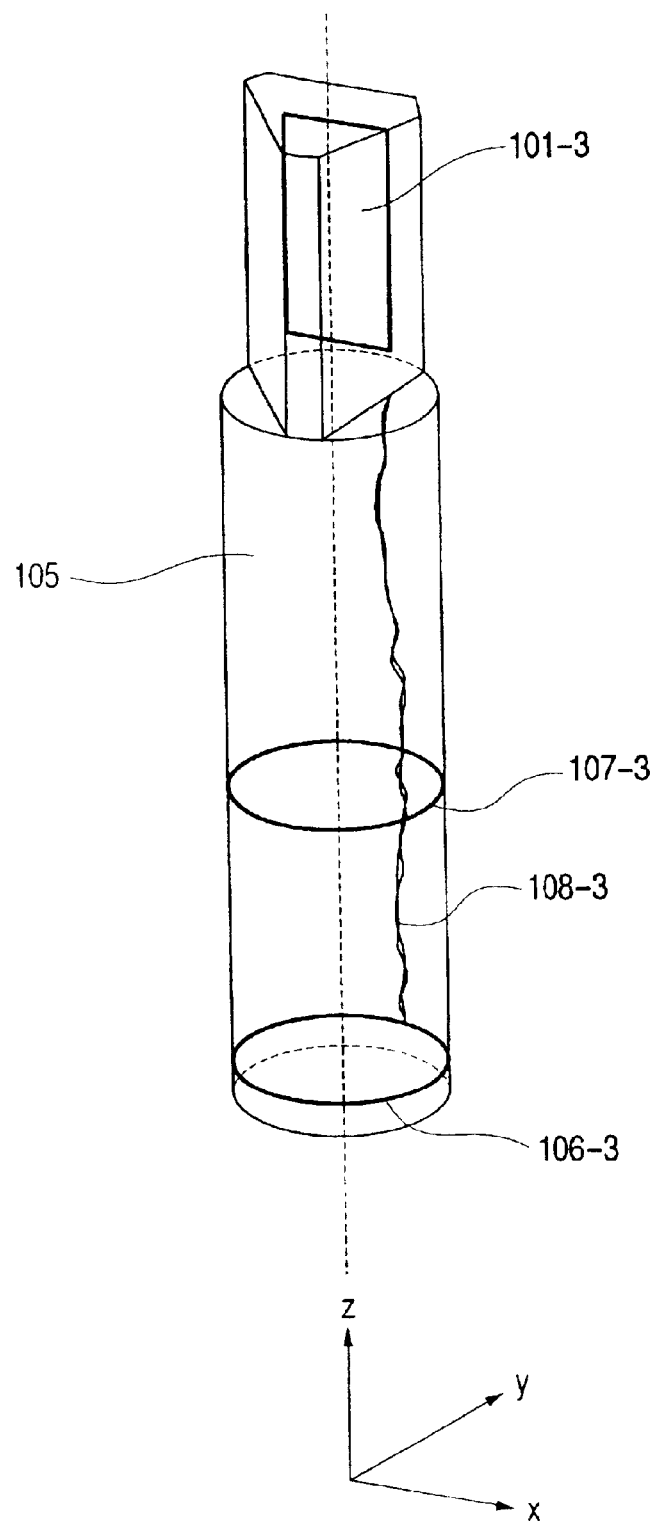
FIG. 5 is a drawing showing the structure of the vector magnetometer of the second embodiment of this invention.

The magnetometers for measuring the magnetic field components respectively in the X, Y and Z directions are shown separately in FIGS. 3, 4, and 5. FIG. 2 shows that each magnetometer in FIGS. 3, 4, 5 is formed into an integrated piece with the coil bobbin 105. The detector coil 106-1 and the compensation coil 107-1 are connected in series by a wire 108-1 to constitute a primary differential coil, and are connected to the input coil connection 104-1 of a SQUID 102-1 fabricated of thin film. The detector coil 106-2 and the compensation coil 107-2 are connected in series by a wire 108-2 to constitute a primary differential coil, and are connected to the input coil connection 104-2 of a SQUID 102-2 fabricated of thin film. The detector coil 106-3 and the compensation coil 107-3 are connected in series by a wire 108-3 to constitute a primary differential coil, and are connected to the input coil connection 104-3 of a SQUID 102-3 fabricated of thin film.

The detection coil 106-3 for detecting the magnetic field component $B_Z$ in the Z direction is installed along the outer circumference of the coil bobbin 105. The detection coil 106-1 for detecting the magnetic field component $B_X$ in the X direction is formed in a four-sided shape installed along the outer circumference along the Y direction parallel to the bottom of the coil bobbin 105 by means of two holes drilled along the diameter. The detection coil 106-2 for detecting the magnetic field component $B_Y$ in the Y direction is formed in a four-sided shape installed along the outer circumference along the X direction parallel to the bottom of the coil bobbin 105 by means of two holes drilled along the diameter. In other words, the surface forming the detection coil 106-1 for detecting the magnetic field component $B_X$ along the X direction intersects with the surface forming the detection coil 106-2 for detecting themagnetic field component $B_Y$ along the Y direction. The $B_X$ component in the X direction and the $B_Y$ component in the Y direction can be measured independently.

A three-sided beam with a common axis is formed along a portion of the longitudinal (Z axis) direction of the tubular shaped coil bobbin 105. In other words, a figure is formed from the first, second and third sides each having a rectangular shape facing the longitudinal axis of the coil bobbin 105. On the first surface are installed the input coil connection 104-1 for SQUID 102-1 and SQUID 102-1 as well as the SQUID mounting plate 101-1 on which is installed the cable connector 103-1. On the second surface are installed the input coil connection 104-2 for SQUID 102-2 as well as the SQUID mounting plate 101-2 on which is installed the cable connector 103-2. On the third surface are installed the input coil connection 104-3 (not shown in the drawing) for SQUID 102-3 and SQUID 102-3 as well as the SQUID mounting plate 101-3 on which is installed the cable connector 102-3 (not shown in the drawing). The cable connectors 103-1, 103-2 and 103-3 are for connecting the output of each SQUID to an FLL circuit 9 installed outside of the Dewar's vessel.

The magnitude (size) of the magnetic field vector, in other words, $\sqrt{(B_X^2+B_Y^2+B_Z^2)}$ is synthesized and found from the magnetic field components $B_X$, $B_Y$, $B_Z$ in the three directions simultaneously measured by the vector magnetometers. The result is displayed on a magnetic field magnitude distribution graph used as the display means and changes over time of the intensity of the magnetic vectors are then monitored.

Figure 6:
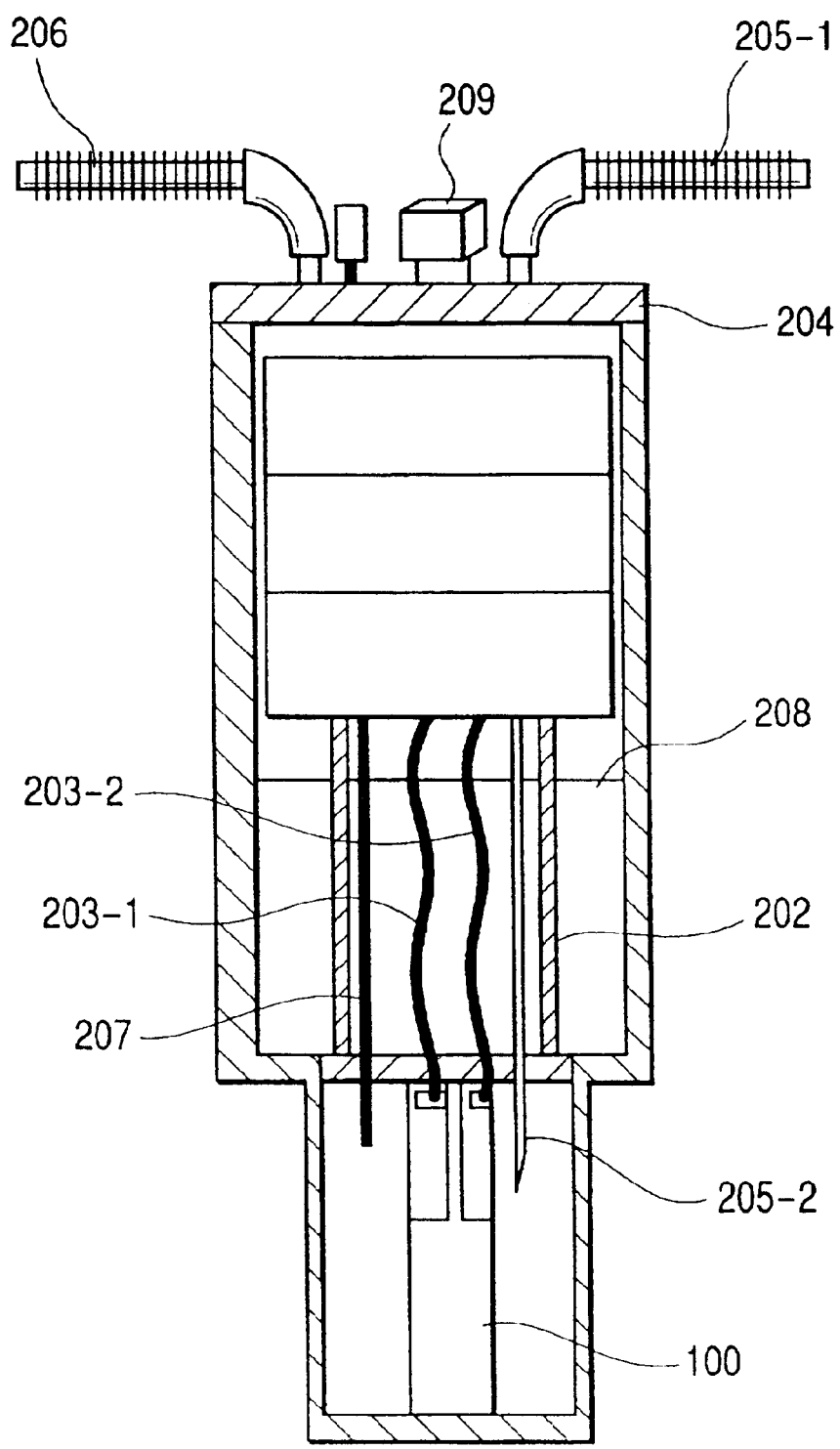
FIG. 6 is a drawing showing the internal layout of the Dewar's vessel containing the vector magnetometer of the second embodiment of this invention.

FIG. 6 is a drawing showing the placement of the vector magnetometers in the interior of the Dewar's vessel. A vector magnetometer 100 is installed at the bottom of the Dewar's vessel 4 as shown in FIG. 2 at the point nearest to the organism to be measured. A more detailed analysis of the magnetic field generating source can be obtained by installing a plurality of vector magnetometers 100 in the bottom of a Dewar's vessel 4 having an enlarged surface area. The magnetometer is supported by an insert 202 of glass-reinforced epoxy resin (FRP or fiber reinforced plastic). In the insert 202, a sensor cable 203-1 (for X axis), sensor cable 203-2 (for Y-axis) and a sensor cable 203-3 (for Z axis not shown in drawing) are installed to electrically connect between the vector magnetometer 100 and the FLL circuit 9. In the top of the insert 202, a flange 204 is installed forming the lid of the Dewar's vessel 4, and a supply port for liquid helium 205-1 and a duct for helium gas 206 are installed on the top of the insert 202. The liquid helium transits the supply port for liquid helium 205-1 and is supplied to the Dewar's vessel 4 from the drain port for liquid helium 205-2. A liquid helium level sensor 207 for detecting the quantity of remaining liquid helium is inserted into the Dewar's vessel 4. Based on a signal from this liquid helium level sensor 207, a fixed level of liquid helium 208 is maintained at to keep a constant liquid helium level 208 supplied to the interior of the Dewar's vessel 4. The cable for the vector magnetometer 100 drawn out from the interior of the Dewar's vessel 4 is installed to couple the external connector 209 to the cable from the FLL circuit 9.

Third Embodiment

Hereafter, measurement of the magnetic field generated by a current dipole magnetic field measurement device and evaluation of the results will be described using the magnetic field measurement method and magnetic field measurement apparatus as explained in the first and second embodiments of this invention with a current dipole formed in the uniform conductor element (electrolytic solution).

Figure 7:
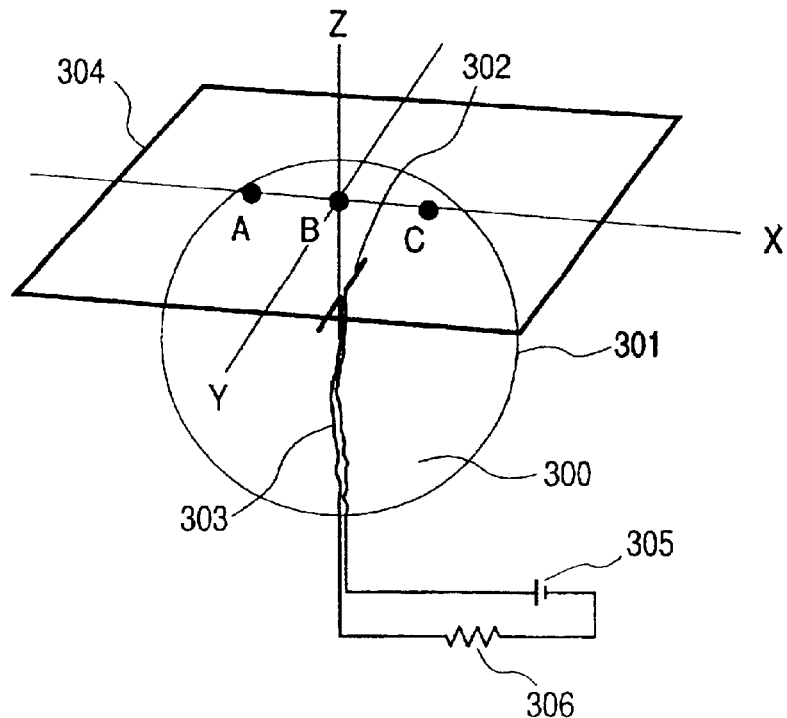
FIG. 7 is a drawing showing the circuit comprising the current dipole in the sphere filled with electrolytic solution and the measurement plane for measuring the magnetic field generated by the current dipole in the third embodiment of this invention.

A drawing of the measurement plane for measuring the magnetic field generated by the current dipole and the circuit forming the current dipole in the sphere filled with electrolytic solution is shown in FIG. 7. A twisted pair line 303 for electrical wiring and including a power supply 305 and a resistor 306 is inserted inside the sphere 301 (Sphere is of acrylic resin material with a diameter of 5 cm.) filled with electrolytic solution 300 (1 mol of NaCl solution) as the uniform conductor element as shown in FIG. 7. The current dipole 302 forms a cutoff section facing the tip of the twisted pair line 303 for electrical wiring purposes. When electrical current flows into the twisted pair line 303 from an external source, an opposite flow of current in twisted pair line 303 cancels out the magnetic field occurring due to the electrical current flow. However, in the portion spreading out on both of the tips, current flow is established in one direction and electrical current spreads through the conducting element from the cutoff section of the other end and returns to the cutoff section at the other end. These cut sections form a structure facing each other, and the tip of the opposing cutoff section has a power source for maintaining a small but constant electrical current in the conducting element. At the measurement plane 304 as shown in FIG. 7, the distribution of the magnetic field generated by the current dipole 302 is measured at the external section of sphere 301 (conducting sphere) filled with electrolytic solution 300. The measurement plane 304 is connected to the sphere 301 at point B as shown in FIG. 7.

Figure 8:
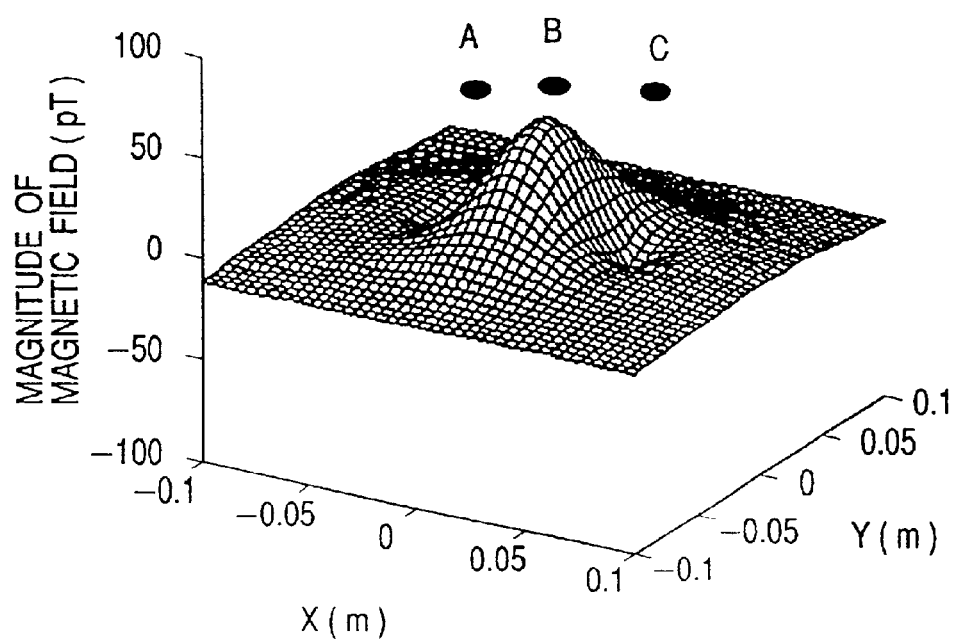
FIG. 8 is a magnetic field magnitude distribution graph of $\sqrt{(B_x^2+B_y^2)}$ magnetic field magnitude indicating the tangential (parallel) components obtained by measuring and synthesizing the magnetic components $B_X$, $B_Y$, in the X and Y directions of the magnetic field generated by the current dipole in the third embodiment of this invention.

FIG. 8 is a magnetic field magnitude distribution graph showing magnetic field magnitude in other words $\sqrt{(B_X^2+B_Y^2)}$ indicating the tangential (parallel) components obtained by measuring with vector magnetometers the magnetic components $B_X$, $B_Y$, in the X and Y directions and synthesizing the result for the magnetic field obtained by the vector magnetometer in FIG. 2 generated by the current dipole shown in FIG. 7. The data for each point shown in FIG. 8 is the result of data measured and analyzed by moving the Dewar's vessel around numerous points (A total of 100 points from points measured on a matrix of 10 points in the X direction and 10 points in the Y direction) on the measurement plane 304. The points A, B and C shown in FIG. 8 correspond to the points A, B and C in FIG. 7, and the origin point (0,0) corresponds to point B shown in FIG. 7. The values of the X and Y axes are shown in units of meters for position points on the measurement plane. The magnetic magnitude distribution thus obtained, has a tangential portion of the magnetic magnitude distribution showing a pattern having a peak directly above the current dipole. This reveals that the center line connecting the center of the (conductive) sphere 301 with the current dipole 302 and the intersection with the measurement plane 304 is the point of maximum magnetic field magnitude (strength). Accordingly, it was found the magnetic field magnitude measured at each point will vary when making measurements at the points A, B and C shown in FIG. 7.

Figure 9:
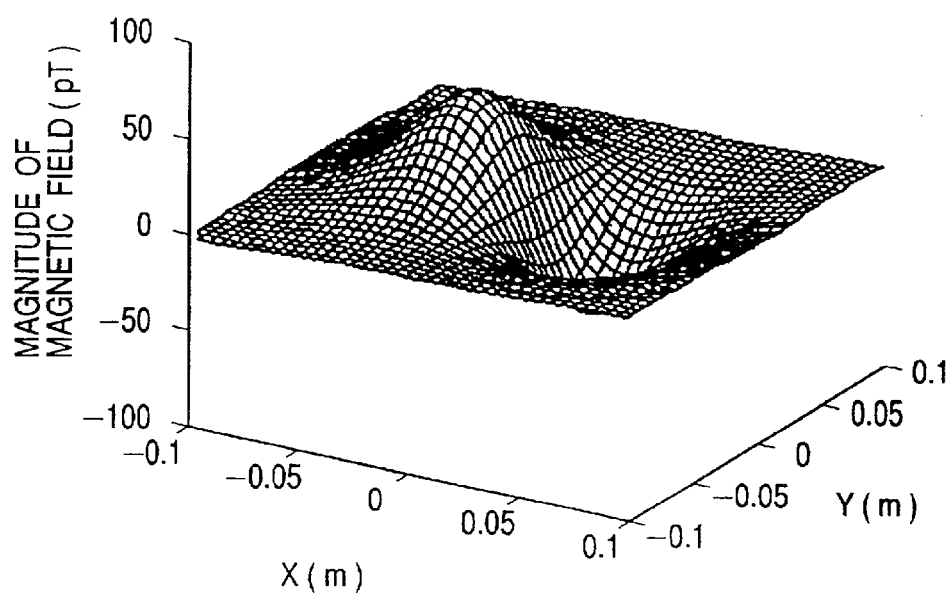
FIG. 9 is a magnetic field magnitude distribution graph of Z direction magnetic component $B_Z$ of the normal line component of the magnetic field generated by the current dipole in the third embodiment of this invention.

FIG. 9 is a magnetic field magnitude distribution graph measured with the apparatus of this invention. The figure shows a magnetic field magnitude distribution graph of the Z direction magnetic component $B_z$ of the normal line component of the magnetic field generated by the current dipole shown in FIG. 7.

The data for each point shown in FIG. 9 is the result of analysis of data measured at a plurality of points (A total of 100 points from points measured on a matrix of 10 points in the X direction and 10 points in the Y direction) while moving the Dewar's vessel 4 over the measurement plane 304. The points A, B and C shown in FIG. 9 correspond to the points A, B and C in FIG. 7, and the origin point (0,0) corresponds to point B shown in FIG. 7. The values of the X and Y axes are shown in units of meters for position points on the measurement plane. As described above, the tangential portion of the magnetic magnitude distribution pattern contained a peak directly above the current dipole however as shown in FIG. 9, the magnetic magnitude distribution for the normal line component $B_z$ shows a pattern having both positive and negative polarity characteristics at a position separated from the current dipole. FIG. 9 showed that large changes in magnetic magnitude were also measured at the points A, B and C and in particular, the magnetic field magnitude reached zero at point B directly above the current dipole which was greatly different from the magnetic field magnitude at point B directly above the current dipole in the tangential portion of the magnetic field magnitude distribution chart of FIG. 8.

The large difference between the tangential and normal line magnetic field magnitude distribution charts for positions where the size of the magnetic magnitude is measured as strong and also the large difference in areas occupied where the magnetic magnitude is strong presents problems during use. In other words, in measurements of a magnetic field in one direction by means of the conventional art, there is clearly a large variation in the time waveform of magnetic field components due to the difference in detection of the magnetic field of the subject being measured.

Figure 10:
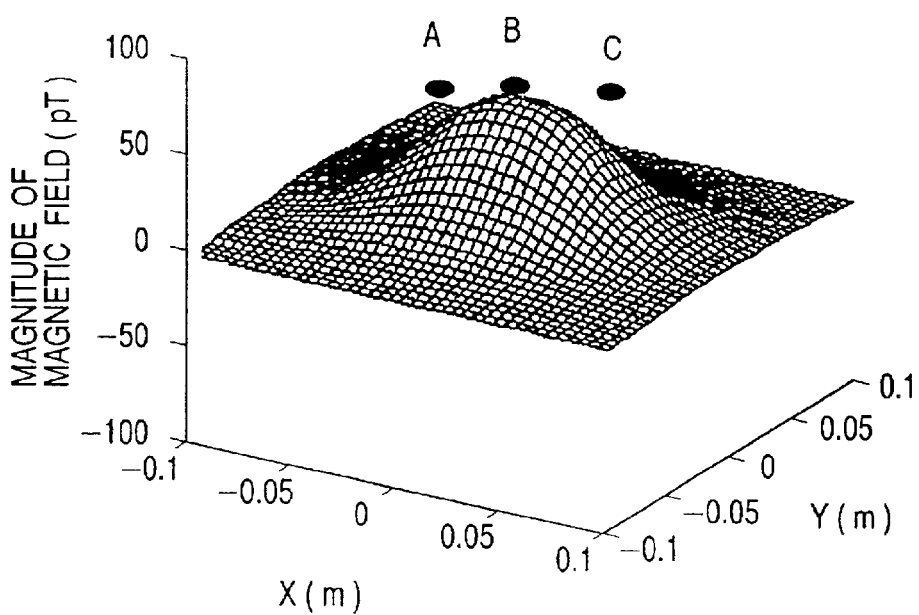
FIG. 10 is a magnetic field magnitude distribution graph of $\sqrt{(B_x^2+B_y^2+B_z^2)}$ magnetic field vector magnitude obtained by measuring and synthesizing the magnetic components $B_X$, $B_Y$, $B_Z$ in the X and Y and Z directions of the magnetic field generated by the current dipole in the third embodiment of this invention.

FIG. 10 is a magnetic field magnitude distribution graph showing the distribution (indicating the intensity of magnetic field vector (size)) (in other words, $\sqrt{(B_x^2+B_y^2+B_z^2)}$) obtained by measuring with vector magnetometers the magnetic components $B_X$, $B_Y$, $B_Z$ in the X and Y, z directions and synthesizing the result for the magnetic field in FIG. 2, generated by the current dipole shown in FIG. 7. The data for each point shown in FIG. 10 is the result of data measured and analyzed by moving the Dewar's vessel 4 around numerous points (a total of 100 points from points measured on a matrix of 10 points in the X direction and 10 points in the Y direction) on the measurement plane 304. The points A, B and C shown in FIG. 10 correspond to the points A, B and C in FIG. 7, and the origin point (0,0) corresponds to point B shown in FIG. 7. The X and Y axis values are shown in units of meters for position points within the measurement plane 304. On comparing the magnetic field magnitude distribution graphs in FIG. 8 and FIG. 9; the magnetic field magnitude distribution graph of FIG. 10 reveals a clearly wide magnetic field of strong intensity (magnitude) compared to the distribution graphs in FIG. 8 and FIG. 9.

The magnetic field magnitude shows large differences at points A, B and C in the magnetic field magnitude distribution graphs of FIG. 8 and FIG. 9, however in FIG. 10, the magnitude (intensity) of the magnetic field is virtually the same for points A, B and C. This result demonstrates that if the distribution of the magnetic field magnitude distribution graph of FIG. 10 is used, in other words $\sqrt{(B_X^2+B_Y^2+B_Z^2)}$ is used, no large changes will occur in the magnitude of the magnetic intensity (magnitude) obtained even if the positions of the subject for measurement (here, an electrical current source) and the magnetometer (measurement position) are changed.

Fourth Embodiment

Sample results from measurement of magnetic fields generated by electrical current sources maintaining a constant current flow were explained in FIG. 8, FIG. 9 and FIG. 10. Hereafter, results from measurement of changes over time in the magnetic field generated by the heart of a fetus will be explained.

Figure 11:
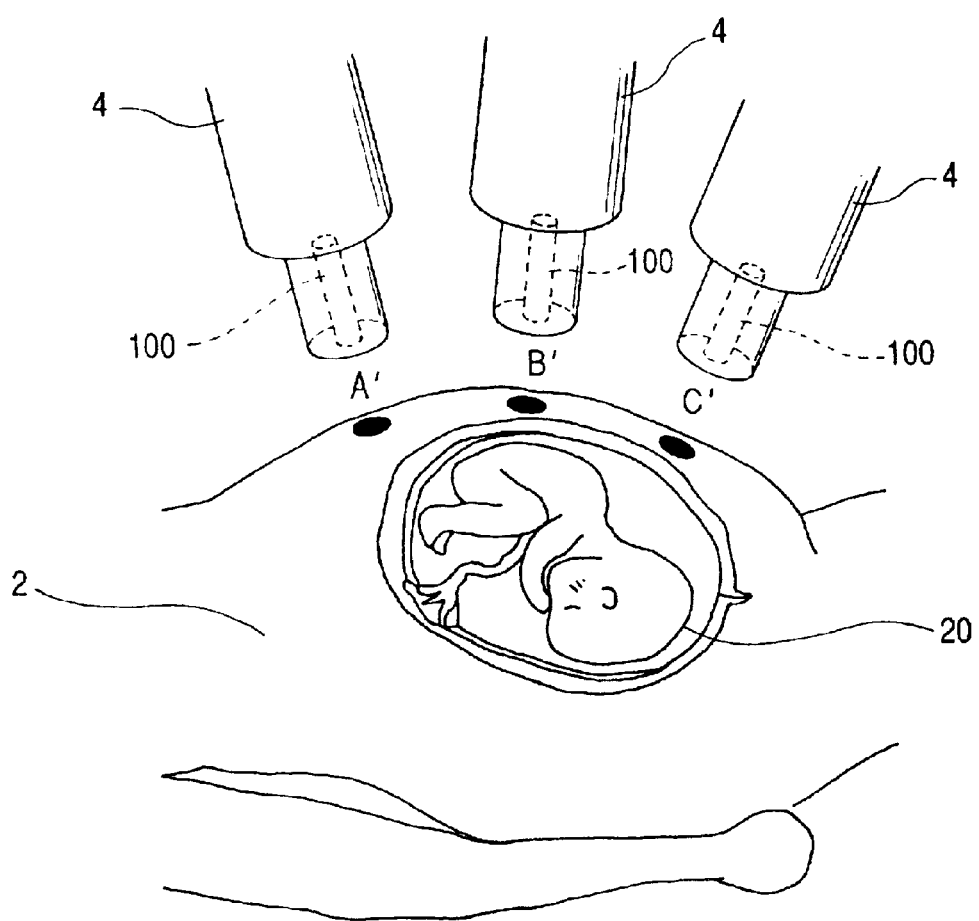
FIG. 11 is a drawing showing a typical position relation of the body of the mother, the fetus, and the bottom position of the tip of the Dewar's vessel housing the vector magnetometer in the fourth embodiment of this invention.

FIG. 11 shows a typical positional relationship of the body of the mother, the fetus and the bottom position of the tip of the Dewar's vessel housing the vector magnetometers shown in FIG. 2. Typical position relations of the bottom position of the tip of the Dewar's vessel 4 housing the vector magnetometers 100, the mother's body 2 and the fetus 20 are shown in FIG. 11. The magnetic field of the heart of the fetus 20 was detected at points A', B', C' in the belly of the mother's body 2 for the magnetic field components $B_X$, $B_Y$, $B_Z$ in the X, Y and Z axis directions. Vertical (up/down) movement control by means of an elevator mechanism 7 of the bed in which the mother's body 2 is laying, and variable control of the angle and position of the bottom of the Dewar's vessel 4 by use of the holding means 5 allow changing the distance between the center position of the bottom of the Dewar's vessel 4 and each point (point A', B') for the belly of the mother's body 2, to allow the center position of the Dewar's vessel 4 to approach each point. The points A', B', C' are separated from each other by a distance of 3 centimeters. A time waveform showing the magnetic field generated by the pulsation of the heart of the fetus for the points A', B', C' are shown in FIG. 12, FIG. 13 and FIG. 14.

Figure 12A:
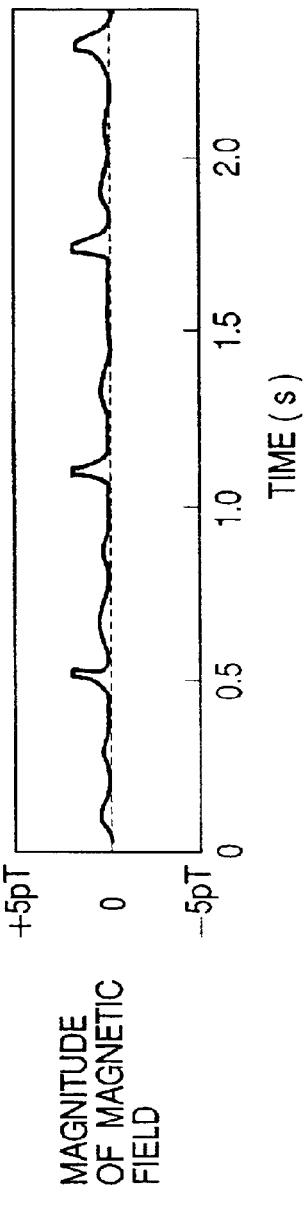
FIGS. 12A, 12B and 12C are time waveforms of the magnetic field magnitude $\sqrt{(B_x^2+B_y^2)}$ expressing the tangential (parallel) components obtained by measuring and synthesizing the magnetic components $B_X$, $B_Y$, in the X and Y and Z directions shown by points A', B', C' in FIG. 11 for the magnetic field generated by the heart of the fetus in the fourth embodiment of this invention.
Figure 12B:
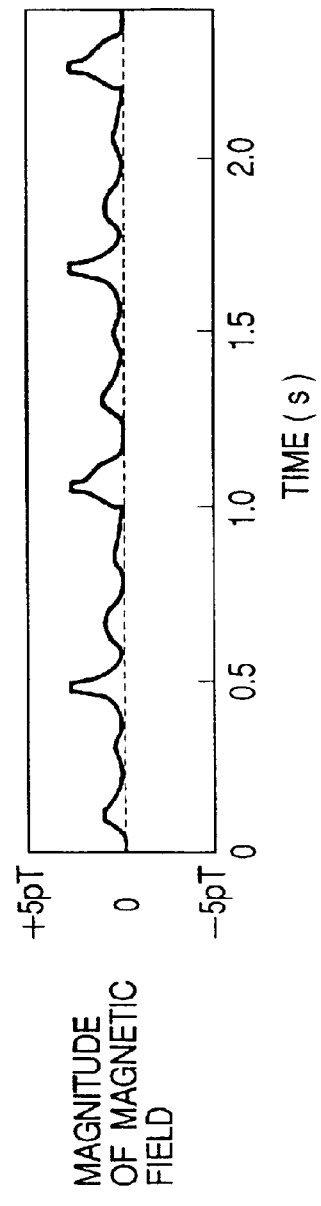
Figure 12C:
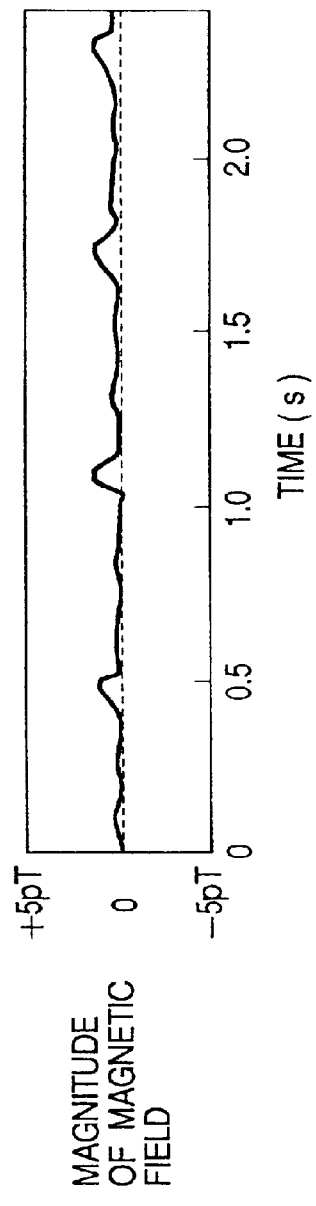

FIGS. 12A, 12B, 12C are time waveforms of $\sqrt{(B_X^2+B_Y^2)}$ indicating the magnetic field magnitude of the tangential (parallel) components obtained by measuring with vector magnetometers shown in FIG. 2 of the magnetic components $B_X$, $B_Y$, in the X and Y directions of the magnetic field generated by the heart of the fetus as measured at the points A', B', C' and synthesizing the result. In other words, FIG. 12 shows a time waveform of $\sqrt{(B_X^2+B_Y^2)}$ for a synthesis of the magnetic components $B_X$, $B_Y$ of a magnetic field parallel to the belly. As is clearly shown from the results in FIG. 12, the time waveforms obtained at the points A' B' C' of FIG. 11 differ largely from one another.

Figure 13A:
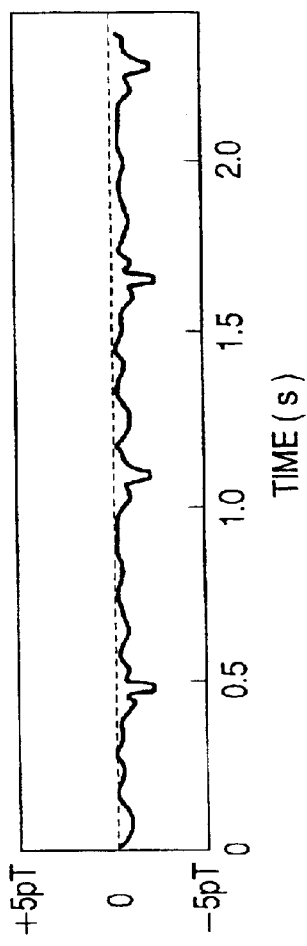
FIGS. 13A, 13B and 13C are time waveforms of the Z direction magnetic field $B_Z$ expressing the normal line components of the magnetic field generated by the heart of the fetus and measured at points A', B', C' in FIG. 11 for the fourth embodiment of this invention.
Figure 13B:
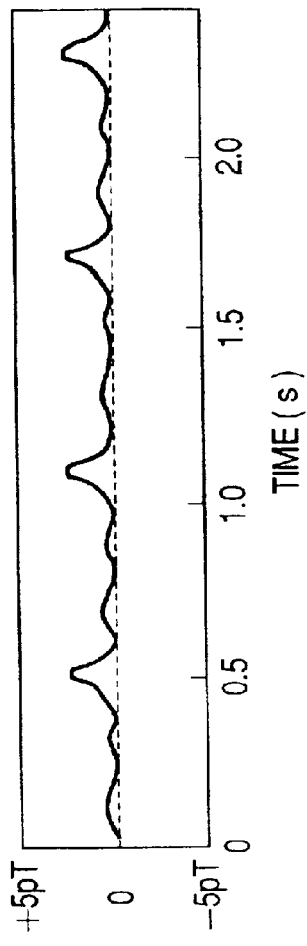
Figure 13C:
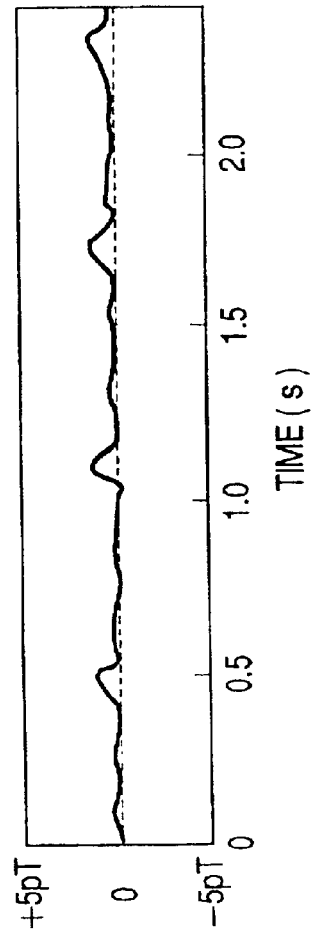

FIGS. 13A, 13B, 13C are time waveforms of the magnetic field obtained by measurement of points A' B' C' of FIG. 11 by means of the vector magnetometers shown in FIG. 2 for this embodiment. These figures show time waveforms for the magnetic component $B_Z$ in the Z axis direction expressing the normal line component of the magnetic field from the heart of the fetus. As shown in the results in FIG. 13, the time waveforms for the Z axis magnetic field component $B_Z$ obtained at the points A' B' C' of FIG. 11 differ largely from one another, in other words the same results as shown in FIG. 11.

Figure 14A:
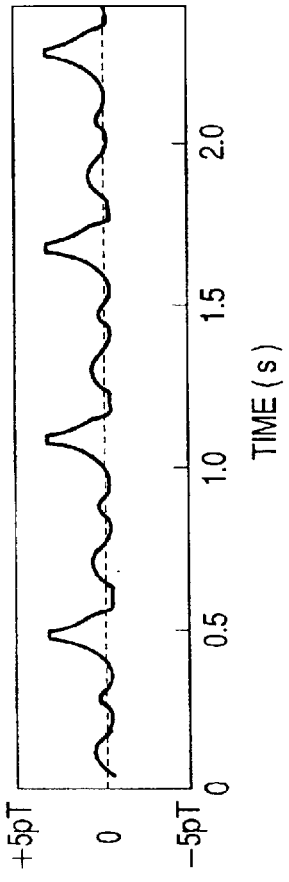
FIGS. 14A, 14B and 14C are time waveforms of the magnetic field vector magnitude $\sqrt{(B_x^2+B_y^2)}$ obtained by measuring and synthesizing the magnetic components $B_X$, $B_Y$, $B_Z$ in the X and Y and Z directions at points A', B', C' in FIG. 11 for the magnetic field generated by the heart of the fetus in the fourth embodiment of this invention.
Figure 14B:
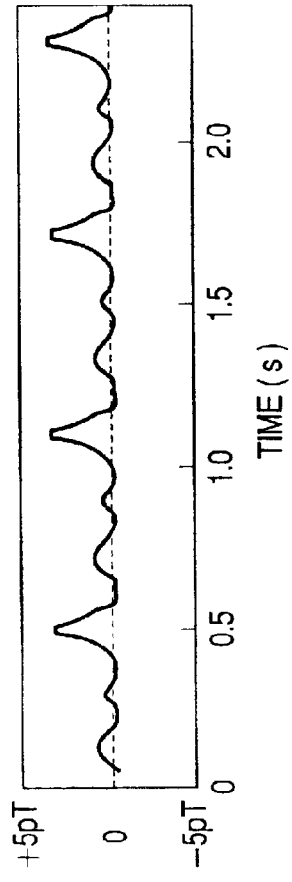
Figure 14C:
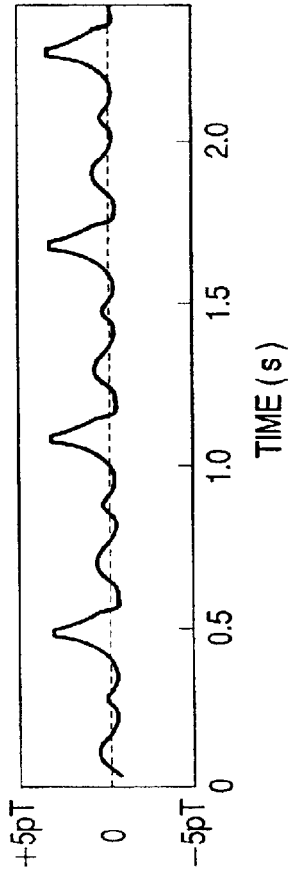

FIGS. 14A, 14B, 14C are time waveforms of $\sqrt{(B_X^2+B_Y^2+B_Z^2)}$ measuring the magnetic components $B_X$, $B_Y$, $B_Z$ in the X, Y and Z directions of the magnetic field generated by the heart of the fetus as measured at the points A' B' C' in FIG. 11 with the vector magnetometers shown in FIG. 2 and synthesizing the result. The time waveforms for $\sqrt{(B_X^{22}+B_Y^2+B_Z^2)}$ magnitude (intensity) obtained by synthesizing the magnetic field components in three directions as shown in FIG. 14, are not significantly dependent on the locations where the magnetic field was detected, and time waveforms were obtained which largely accompanies the same changes over time. In other words, by detecting the magnetic field components $B_X$, $B_Y$, $B_Z$ in the X, Y, Z directions of the magnetic field from the heart of the fetus and synthesizing the results, or in other words by synthesizing the magnitude (size) of the magnetic field vectors, time waveforms can be obtained that largely correspond to the changes over time without depending on the position for detecting $B_X$, $B_Y$, $B_Z$ magnetic field components in the X, Y and Z axis directions of the magnetic field generated by the heart of the fetus. Thus, changes over time in the magnetic field from the heart of the fetus can be satisfactorily and accurately detected within a wide range.

Fifth Embodiment

Figure 15A:
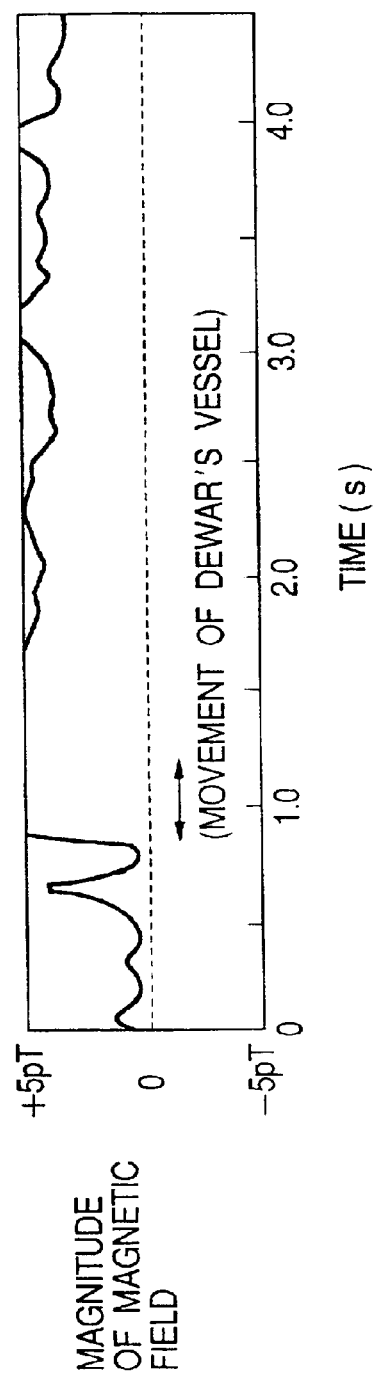
FIGS. 15A and 15B are time waveforms of the magnetic field vector magnitude $\sqrt{(B_x^2+B_y^2+B_z^2)}$ obtained by measuring synthesizing the magnetic components $B_X$, $B_Y$, $B_Z$ in the X and Y and Z directions detected by the vector magnetometers in FIG. 2 from the magnetic field generated by the heart of the fetus while moving the Dewar's vessel in the fifth embodiment of this invention.
Figure 15B:
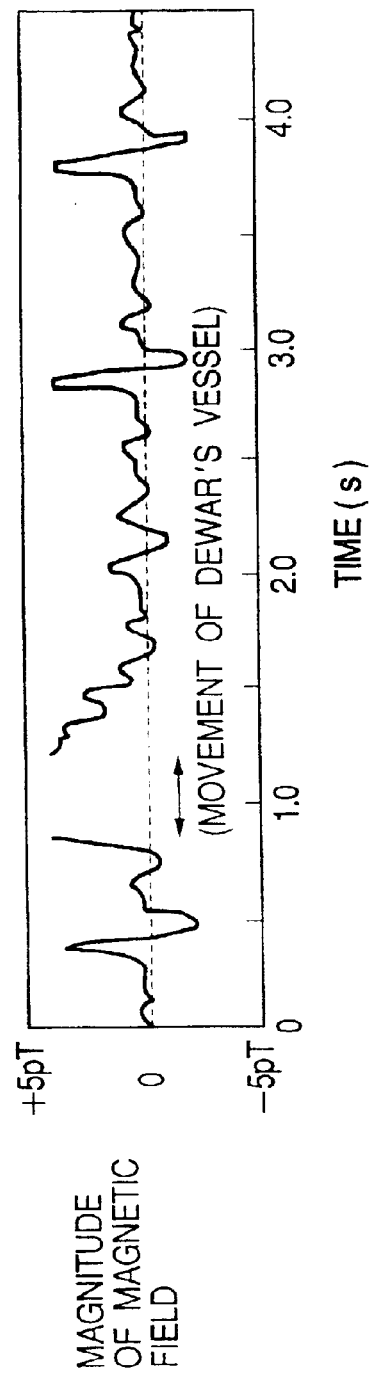

FIGS. 15A and 15B are time waveforms of $\sqrt{(B_X^2+B_Y^2+B_Z^2)}$ magnitude (size) of the magnetic field vectors obtained from synthesizing the result after measuring the magnetic fields $B_X$, $B_Y$ and $B_Z$ in the X, Y and Z directions while moving the Dewar's vessel to measure with the magnetometers of FIG. 2 for this embodiment, the magnetic fields $B_X$, $B_Y$ and $B_Z$ in the X, Y and Z directions of the magnetic field generated by the heart of the fetus. The effect the frequency of the filter 10 exerts on the time waveform for $\sqrt{(B_X^2+B_Y^2+B_Z^2)}$ is shown in FIG. 15A and FIG. 15B. Fluctuations of the time waveform for $\sqrt{(B_X^2+B_Y^2+B_Z^2)}$ of FIG. 15A and FIG. 15B are shown on the waveform display monitor when searching for the ideal location during measurement of the magnetic field generated by the heart of the fetus. FIG. 15A shows a typical time waveform output from the waveform display monitor when the signal sent to the computer 11 is tapped off and the tapped signal passed through a 0.05 Hz–100 Hz band filter. A large drift appears in the time waveform when the Dewar's vessel 4 is moved in a time band (approximately 200 milliseconds) shown by the horizontal arrow in FIG. 15A. Also, a long time of a several dozen seconds is required for the time waveform to stabilize even after the Dewar's vessel 4 has stopped and an extremely long time was required to search out an ideal location. FIG. 15B shows a typical time waveform output from the waveform display monitor when the signal sent to the computer 11 is tapped off and the tapped signal passed through a highpass filter allowing signals greater than or equal to 5 Hz to pass through. The signal that passed through the 0.05 Hz–100 Hz band filter was sent to the computer. The drift on the time waveform shown on FIG. 15B was small when the Dewar's vessel 4 was moved and the time waveform immediately stabilized within a short time (approximately 600 milliseconds). By tapping off the signal sent to the computer 11 and applying the tapped signal to a bypass filter allowing signals greater than or equal to 5 Hz to pass through, the Dewar's vessel 4 was then set at an ideal position to allow measurement of the magnetic field generated by the heart of the fetus. The signal input to the computer 11 contained the required frequency band and did not cause any problems.

Sixth Embodiment

The magnetic field measurement method and the magnetic field measurement apparatus that is described in the first and second embodiments explained methods suitable for detecting of impurities having magnetic properties inside a nonmagnetic metal wire. The metal SUS316 is nonmagnetic however exhibits magnetic properties when made to contain impurities of iron, nickel or chromium and preferably these impurities should be detected with a nondestructive method.

Figure 16:
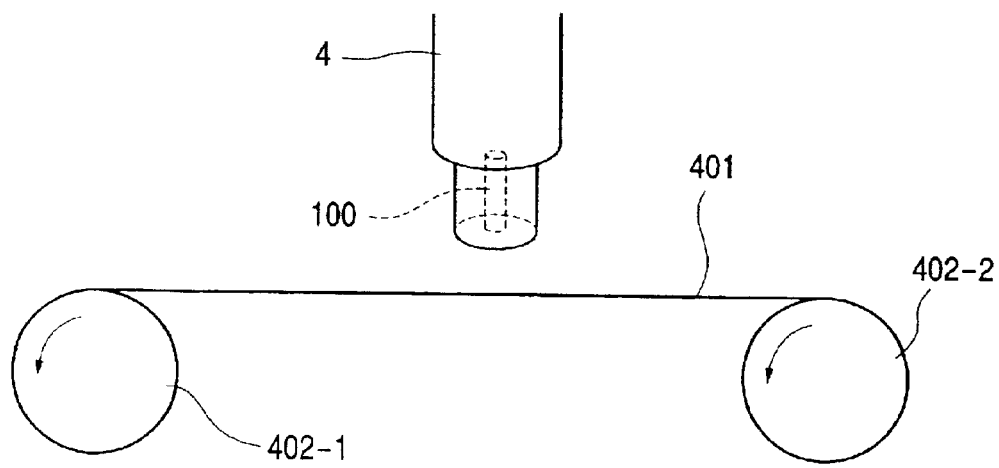
FIG. 16 is a concept view showing detection of magnetized impurities in a nonmagnetic metallic wire in the sixth embodiment of this invention.

FIG. 16 is a concept view showing a method for detection of magnetized impurities in a nonmagnetic metallic wire utilizing the magnetic field measurement apparatus described in the first and second embodiments of this invention. A nonmagnetic metallic wire 401 is installed near the bottom of the Dewar's vessel 4 containing the vector magnetometer 100. The nonmagnetic metallic wire 401 is wound from the rotating reel 402-2 onto the rotating reel 402-1 by the rotation of the rotating reels 402-1 and 402-2 in the direction of the arrows. The vector magnetometer 100 detects the magnetic components in three directions of the intersecting magnetic fields from the nonmagnetic metallic wire 401 while being wound on the rotating reel 402-1, synthesizes the results of the magnetic components in three directions and finds the magnetic vector for the magnitude $\sqrt{(B_X^2+B_Y^2+B_Z^2)}$. The nonmagnetic metallic wire 401 is thus scanned in this way and impurities are detected at high speed in a non-destructive manner in the magnetic field of the nonmagnetic metallic wire 401 while the members of the subject for measurement are changed and the Dewar's vessel 4 is moving.

Figure 17:
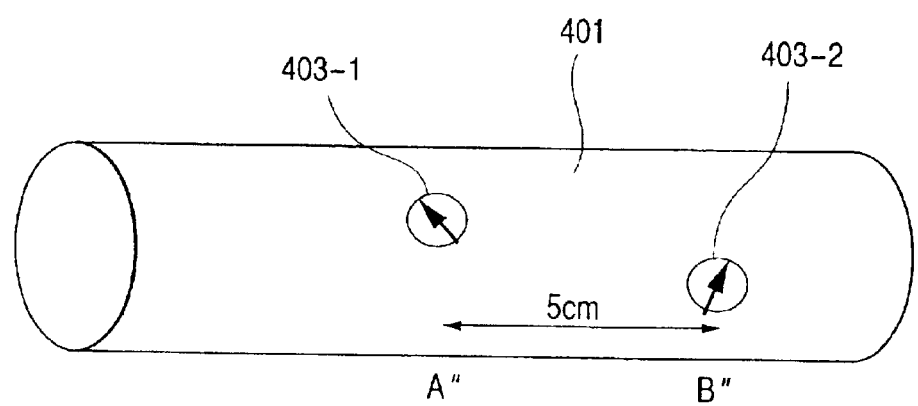
FIG. 17 is an enlarged view of the interior of the nonmagnetic metallic wire containing magnetized impurities in two locations in the sixth embodiment of this invention.
Figure 18:
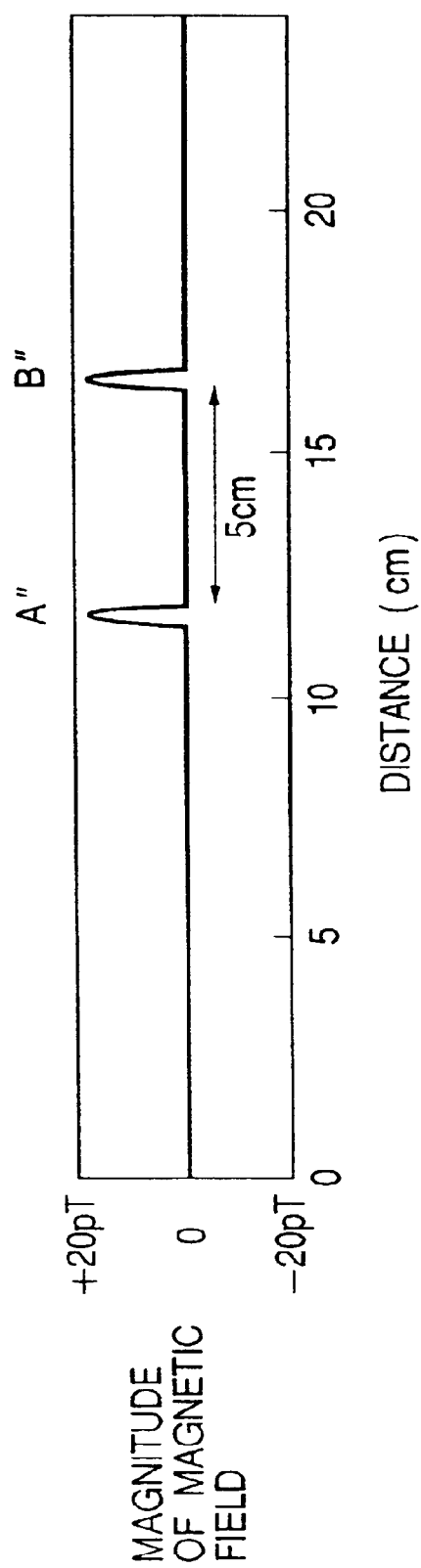
FIG. 18 is a drawing showing the magnetic field vector magnitude of the interior of the nonmagnetic metallic wire containing magnetized impurities in two locations in the sixth embodiment of this invention.

FIG. 17 is an enlarged view of the interior of the nonmagnetic metallic wire containing magnetized impurities in two locations. FIG. 18 is a drawing showing the magnetic field vector magnitude in the interior of the nonmagnetic metallic wire containing magnetized impurities in two locations. Iron impurities 403-1 and 403-2 are doped in a concentration of 1 PPM respectively into in the point A" and the point B" which are separated from each other by five centimeters in the nonmagnetic metallic wire 401. These iron impurities 403-1 and 403-2 are magnetized in respectively different directions. When the nonmagnetic metallic wire 401 shown in FIG. 16, is made to contain the impurities as shown in FIG. 17, a magnetic field vector magnitude $\sqrt{(B_X^2+B_Y^2+B_Z^2)}$ as shown in FIG. 18 is detected by means of the vector magnetometers 100 and the result synthesized. A change in magnitude of the magnetic field vector as shown in FIG. 18, contains the maximum magnitude of the magnetic field vector separated by five centimeters and corresponding to the impurities contained in point A" and point B".

The concentration of magnetized impurities can be quantitatively found by means of the following procedure. A nonmagnetic metallic wire checked beforehand by the vector magnetometer 100 to contain no magnetic impurities is then made to contain a known concentration of magnetic impurities of various types for detection/quantification purposes. The maximum magnitude of the magnetic field vector is found by using the vector magnetometer 100 on this quantification nonmagnetic metallic wire, which is useful as a quantification wire due to the maximum magnitude of the magnetic field vector and to the already known concentration of impurities. The concentration as applicable to the maximum magnitude of the magnetic field vector shown in FIG. 18 can be found by means of inner or outer insertion using the above mentioned quantification wire. The vector Omagnetometer 100 is easily capable of detecting the magnetic field vector intensity (magnitude) of several pT so that impurities can be detected with high sensitivity. Further, as shown in FIG. 18, important characteristics are that the same magnetic field vector magnitude can be obtained even if the impurities have different magnetization directions, and that the same magnetic field magnitude can be obtained if the impurity concentration is the same, regardless of the direction the impurities are magnetized in. The above explanation described detection of magnetized impurities inside a nonmagnetic metallic wire however this invention need not be limited to a nonmagnetic metallic wire and needless to say, can also be applied to detection of magnetized substances in a common nonmagnetic element.

As clearly shown in the explanation of the above embodiment, when for instance a change occurs in an environment in which the subject for examination is placed such as when the mother's body moves and the position of the fetus then changes or for instance when a change in position occurs versus the subject for examination such as for a substance placed inside the subject for examination or when the subject for examination moves; then the magnetic field components $B_X$, $B_Y$, and $B_Z$ are detected in the X, Y and Z axis directions of the magnetic field of the subject for examination and by then synthesizing the $\sqrt{(B_X^2+B_Y^2+B_Z^2)}$ magnetic field vector magnitude (size) from the detection results, time changes from the subject for examination can be accurately detected. For instance, besides a fetus, the growth process in the egg of an animal such as a type of bird, or reptile can be observed and detection performed.

Hereafter, the configuration of this invention is summarized. The magnetic field apparatus of this invention for detecting the magnetic field of the subject for examination is characterized in comprising a single or a plurality of vector magnetometers comprised of detection coils for detecting magnetic fields of three directions and a superconductive quantum interferometer device (SQUID) connected to these detection coils; a display means for displaying the magnetic field magnitude or time waveform of the magnetic field magnitude synthesized from the magnetic field components detected in the three directions by the single or plurality of vector magnetometers, and a control means for controlling the positional relation between the subject for examination and the Dewar's vessel containing the magnetometers. This invention is also characterized by the following points.

(1) Displaying the value or time changes of the value of the magnetic vector magnitude $\sqrt{(B_X^2+B_Y^2+B_Z^2)}$ synthesized after finding the squared sum of the magnetic components in the three directions.

(2) Passing the magnetic field signal containing the synthesized magnetic field magnitude through a high pass filter to remove the low frequency components and display the result on a display means.

(3) After passing the signal for the three directions of the magnetic field components through a high pass filter to remove the low frequency components, displaying the value or the time waveform at that time of the synthesized magnetic field component for the three directions on the display means.

(4) Dividing the signal of the magnetic field components for the three directions detected by means of the vector magnetometers into two signals and synthesizing the magnetic field components in the three directions using one of the two signals, removing the low frequency components by passing the signal through a high pass filter and displaying the result on the display means.

(5) Dividing the signal of the magnetic field components for the three directions detected by means of the vector magnetometers into two signals and passing one of those signals for the magnetic field components in three directions through a high pass filter and after removing the low frequency components, displaying the value or the time waveform at that time of the synthesized magnetic field component for the three directions on the display means.

(6) A coil bobbin made from an insulating piece and holds the three detection coils mounted in three orthogonal directions and having mutually intersecting surfaces, and the center of each detection coil runs along the center axis of the coil bobbin, further, a surface forming one detection coil is perpendicular to the center axis of the coil bobbin, the surfaces forming the other two detection coils intersect and are also parallel to the center axis of the coil bobbin.

(7) The subject for inspection is a fetus inside the mother's body.

(8) The subject for inspection is a magnetized substance within a nonmagnetic material.

What is claimed is:

1. A magnetic field measurement apparatus comprising:

a magnetometer comprising SQUIDs and three detection coils each of which detects each of three orthogonal directional magnetic field components of a magnetic field generated from a fetus in a living body;

a computer which synthesizes the magnitude of the magnetic field by a square sum of said three orthogonal directional magnetic field components of the magnitude field generated from the fetus in the living body; and a display which displays the time variation of a waveform of said magnitude of the synthesized magnetic field;

wherein the signal of each of the three orthogonal directional magnetic field components detected by the magnetometer is divided into two signals, the magnitude of the magnetic field is synthesized by using one of the two signals, and the time variation of waveform of the magnitude of the synthesized magnetic field after passing through a high pass filter is displayed on the display.

2. A magnetic field measurement apparatus according to claim 1, further comprising:

a coil bobbin which comprises an insulator material and holds the three detection coils in three orthogonal directions, respectively;

wherein the three detection coils have planes orthogonal to one other, two of the three detection coils pass through a center axis of the coil bobbin, a plane formed by one of the three detection coils is perpendicular to the center axis of the coil bobbin, and two planes formed by the other two of the three detection coils are orthogonal to each other and are parallel to the center axis of the coil bobbin.

3. A magnetic field measurement apparatus comprising:

a magnetometer comprising SQUIDs and three detection coils each of which detects each of three orthogonal directional magnetic field components of a magnetic field respectively, which are generated from a fetus in a living body;

a computer which synthesizes the magnitude of the magnetic field by a square sum of said three orthogonal directional magnetic field components of the magnitude of the magnetic field generated from the fetus in the living body; and a display which displays the time variation of a waveform of said magnitude of the synthesized magnetic field;

wherein the signal of each of the three orthogonal directional magnetic field components detected by the magnetometer is divided into two signals, the magnitude of the magnetic field is synthesized by using one of the two signals after passing said one of the two signals through a high pass filter, and the time variation of waveform of the magnitude of the synthesized magnetic field is displayed on the display.

4. A magnetic field measurement apparatus according to claim 3, further comprising:

a coil bobbin which comprises an insulator material and holds the three detection coils in three orthogonal directions, respectively;

wherein the three detection coils have planes orthogonal to one other, two of the three detection coils pass through a center axis of the coil bobbin, a plane formed by one of the three detection coils is perpendicular to the center axis of the coil bobbin, and two planes formed by the other two of the three detection coils are orthogonal to each other and are parallel to the center axis of the coil bobbin.

* * * * *